(12) United States Patent
Freeman et al.

(10) Patent No.: US 8,318,088 B2
(45) Date of Patent: Nov. 27, 2012

(54) RADIATION STERILIZATION OF MEDICAL DEVICES

(75) Inventors: Abigail Freeman, Fremont, CA (US);
Brian Riggs, Temecula, CA (US);
Robert Harrison, Perris, CA (US);
Greg Simmons, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/096,892

(22) Filed: Apr. 28, 2011

(65) Prior Publication Data

US 2011/0211990 A1     Sep. 1, 2011

Related U.S. Application Data

(63) Continuation of application No. 11/809,511, filed on Jun. 1, 2007, now Pat. No. 7,959,857.

(51) Int. Cl.
*A61L 2/00* (2006.01)
*B01J 19/08* (2006.01)
*G01T 1/185* (2006.01)
*G01N 21/00* (2006.01)
*H01J 27/00* (2006.01)
*A61B 6/00* (2006.01)
*A61B 5/00* (2006.01)
*A61M 29/00* (2006.01)

(52) U.S. Cl. ......... 422/22; 422/1; 422/186.05; 250/389; 250/427; 250/433; 250/453.11; 250/455.11; 250/492.3; 250/515.1; 600/434; 600/585; 606/191; 606/194; 606/198

(58) Field of Classification Search ............... 422/1, 22, 422/186.05; 250/389, 427, 433, 453.11, 250/455.11, 492.3, 515.1; 600/434, 585; 606/191, 194, 198
See application file for complete search history.

(56) References Cited

U.S. PATENT DOCUMENTS

RE23,195 E * 2/1950 Brasch .............................. 21/54
(Continued)

FOREIGN PATENT DOCUMENTS

EP      1 518 563       3/2005
(Continued)

OTHER PUBLICATIONS

English Machine Translation of JP 2000-334028, 19 pages total (Dec. 5, 2000).

*Primary Examiner* — Jill Warden
*Assistant Examiner* — Monzer Chorbaji
(74) *Attorney, Agent, or Firm* — Squire Sanders (US) LLP

(57) ABSTRACT

A method of radiation sterilizing a plurality of stent-catheter assemblies includes positioning a plurality of stent-catheter assemblies on a fixture, each of the stent catheter assemblies being arranged in a planar configuration and disposed in corresponding planar packages supported on the fixture, wherein the packages are stacked horizontally on the fixture, and wherein the stents of the assemblies are positioned at a position in each package such that the stents are exposed to the same or substantially the same radiation; and exposing the packages to an incoming radiation beam, the radiation beam being at an acute angle to the planes of the planar configuration of the assemblies, wherein the packages are arranged such that a front end of the stack faces the radiation beam and a back end of the stack faces away from the radiation beam.

21 Claims, 11 Drawing Sheets

U.S. PATENT DOCUMENTS

| | | | |
|---|---|---|---|
| 4,656,083 | A | 4/1987 | Hoffman et al. |
| 5,637,113 | A | 6/1997 | Tartaglia et al. |
| 5,765,682 | A | 6/1998 | Bley et al. |
| 5,825,042 | A | 10/1998 | Strobel |
| 6,594,156 | B1 | 7/2003 | Van Antwerp |
| 6,730,923 | B1 * | 5/2004 | May et al. ............... 250/494.1 |
| 6,806,476 | B2 | 10/2004 | Rose et al. |
| 7,776,926 | B1 | 8/2010 | Hossainy et al. |
| 7,959,857 | B2 | 6/2011 | Freeman et al. |
| 8,034,287 | B2 | 10/2011 | Freeman |
| 2003/0215354 | A1 | 11/2003 | Clark et al. |
| 2004/0267347 | A1 | 12/2004 | Cervantes |
| 2005/0013729 | A1 * | 1/2005 | Brown-Skrobot et al. ..... 422/24 |
| 2005/0233062 | A1 * | 10/2005 | Hossainy et al. ............. 427/2.1 |
| 2006/0067974 | A1 * | 3/2006 | Labrecque et al. ........... 424/426 |

FOREIGN PATENT DOCUMENTS

| | | |
|---|---|---|
| JP | 11-133196 | 5/1999 |
| JP | 2000-334028 | 12/2000 |
| JP | 2002-078780 | 3/2002 |
| JP | 2005-249671 | 9/2005 |
| JP | 2008-275991 | 11/2008 |
| WO | WO 03/037390 | 5/2003 |
| WO | WO 2006/034157 | 3/2006 |

* cited by examiner

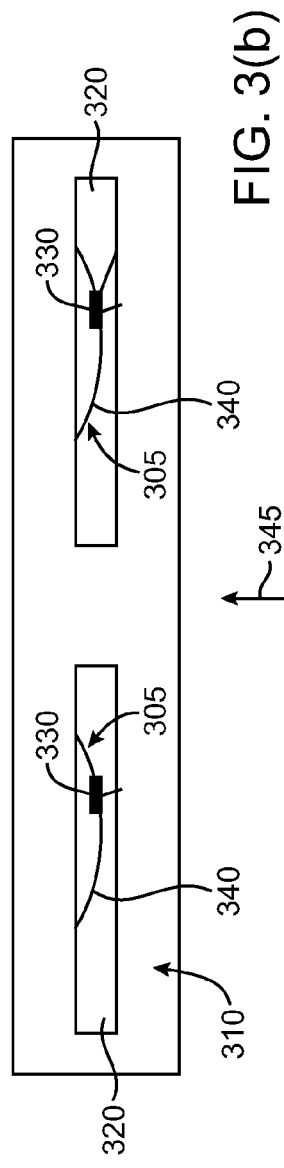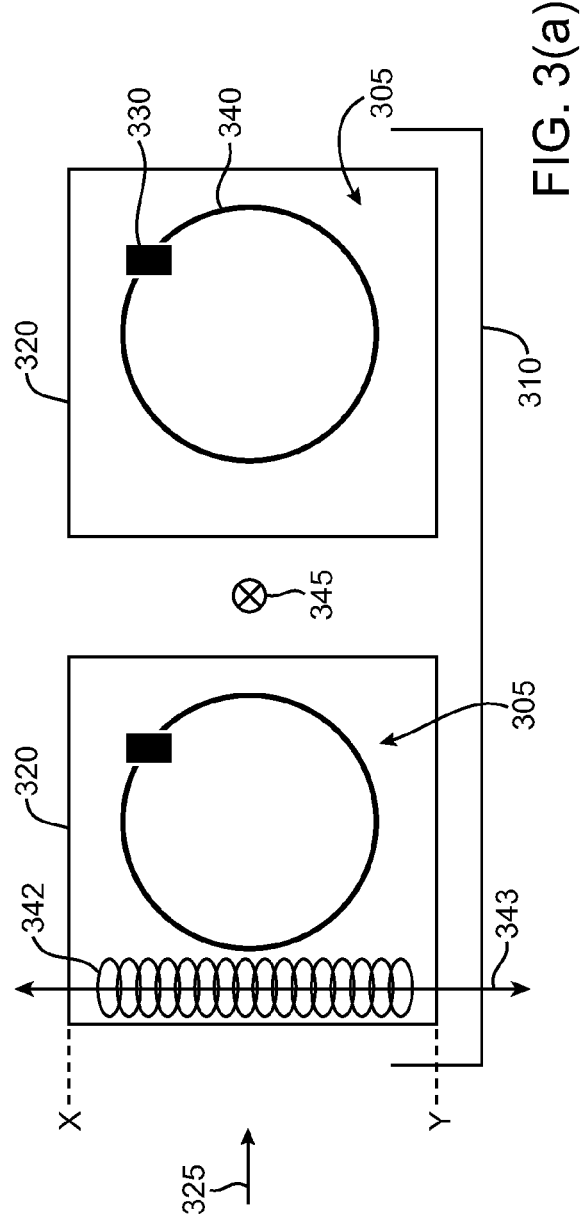

RADIATION STERILIZATION OF MEDICAL DEVICES

This application is a continuation of U.S. patent application Ser. No. 11/809,511, filed Jun. 1, 2007, the entire disclosure of which is incorporated herein by reference.

BACKGROUND OF THE INVENTION

1. Field of the Invention

Disclosed herein are methods and apparatuses for sterilization of medical devices using radiation.

2. Description of the State of the Art

Disclosed herein are radially expandable endoprostheses adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. The polymeric scaffolding may also serve as a carrier of an active agent or drug.

After a stent is fabricated, a stent or a stent-catheter device typically undergoes sterilization to reduce the bioburden of the stent to an acceptable sterility assurance level (SAL). There are numerous methods of sterilizing medical devices such as stents, the most common being ethylene oxide treatment and treatment with ionization radiation such as electron beam (E-beam) and gamma radiation.

There is a desire to make E-beam sterilization commercially feasible for polymeric stents. As medical devices increase in complexity, sterilization process technology becomes imperative. A commercially feasible E-beam sterilization process that is compatible with existing E-beam facilities is desired. Also desired is a fixture apparatus having the capability of processing a large volume of medical devices in a short period of time, robustness to human error, and reproducibility of dose from device to device.

SUMMARY

Various embodiments of the present invention include a method of radiation sterilizing a plurality of stent-catheter assemblies, the method comprising: positioning a plurality of stent-catheter assemblies on a fixture, each of the stent catheter assemblies being arranged in a planar configuration and disposed in corresponding planar packages supported on the fixture, wherein the packages are stacked horizontally on the fixture; and exposing the packages to an incoming radiation beam, the radiation beam being at an acute angle to the planes of the planar configuration of the assemblies, wherein the packages are arranged such that a front end of the stack faces the radiation beam and a back end of the stack faces away from the radiation beam.

Further embodiments of the present invention include a method of radiation sterilizing a plurality of medical devices, the method comprising: positioning a plurality medical devices on a fixture; and exposing the devices to an incoming radiation beam through movement of the plurality of devices with respect to a radiation source, wherein the number of devices through which the radiation beam passes varies with the movement, wherein a radiation shield is positioned such that a variation in radiation exposure among the medical devices from incoming or backscattered radiation is reduced.

BRIEF DESCRIPTION OF THE DRAWINGS

FIG. 3(a) is a schematic illustration of a front view of a fixture for supporting two packages, each package containing a stent-catheter assembly.

FIG. 3(b) depicts an overhead view of a fixture of FIG. 3(a).

DETAILED DESCRIPTION OF THE INVENTION

Radiation sterilization is well known to those of ordinary skill in the art. Medical devices composed in whole or in part of polymers can be sterilized by various kinds of radiation, including, but not limited to, electron beam (E-beam), gamma ray, ultraviolet, infra-red, ion beam, x-ray, and laser sterilization. Generally, it is desirable to increase the throughput of sterilization processes to increase the manufacturing efficiency.

Various embodiments of the present invention relate to the sterilization of multiple medical devices. Such medical devices include implantable medical devices and delivery systems for such devices. The methods described herein may be applied generally to polymeric implantable medical devices, such as for stents, in particular polymeric stents. The methods reduce or narrow the range of radiation exposure from device to device.

Therefore, each device may be irradiated within a specified or selected range. This is of particular importance for polymeric devices, since exposure to radiation above a specified range can cause undesirable degradation of chemical and mechanical properties of a polymer. The methods discussed herein reduce the likelihood of irradiation outside a specified range, causing an undesirable increase in temperature and a corresponding undesirable degree of degradation.

The methods disclosed herein may be applied in combination with a reduced temperature sterilization process in which a device is cooled before, during, and/or after sterilization. The reduced temperature can be below ambient temperature during sterilization. The methods disclosed herein may be applied to a sterilization process using various kinds of radiation.

Examples of implantable medical devices include, but are not limited to, self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure or substrate of the device can be of virtually any design.

Figure 1:
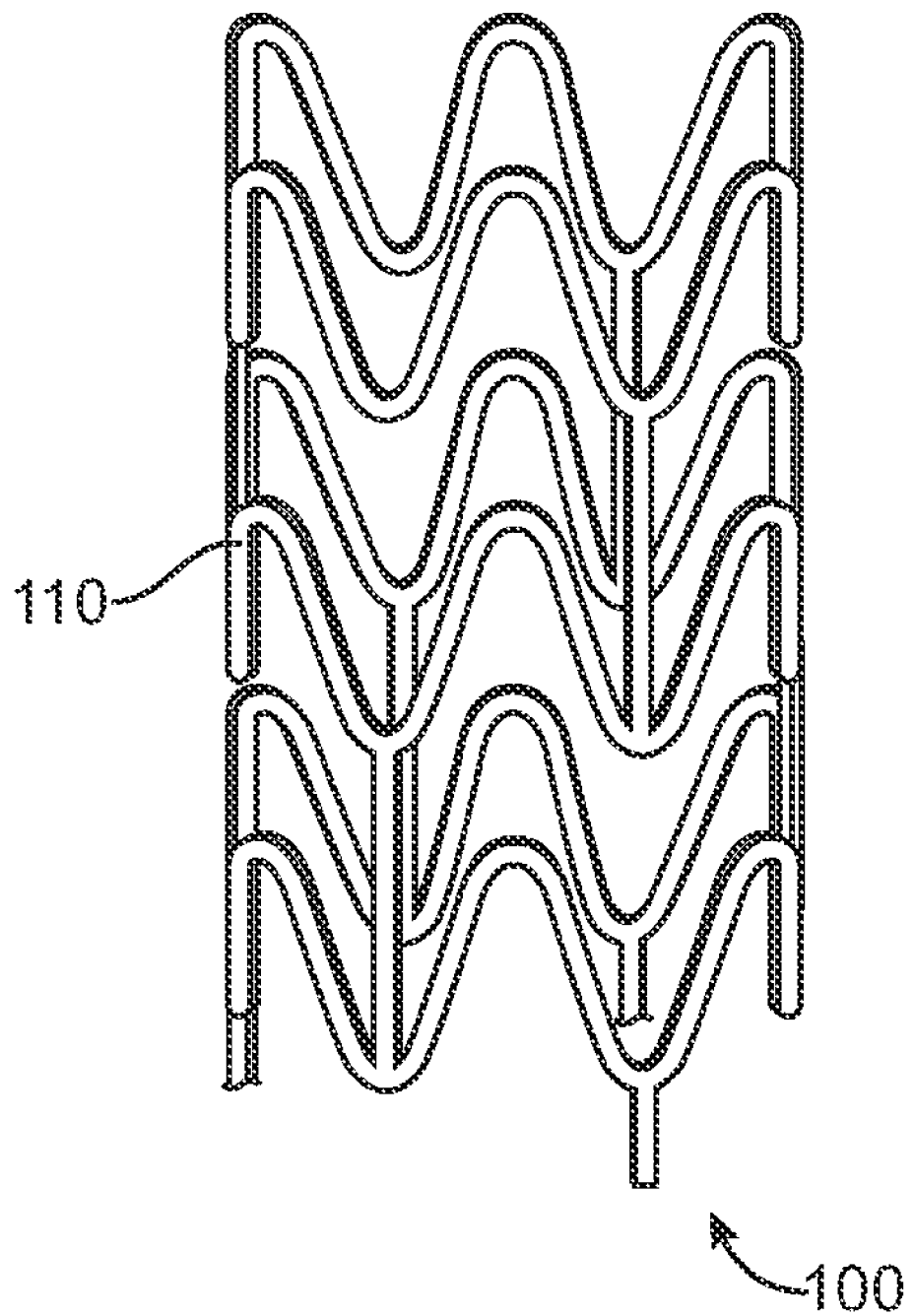
FIG. 1 depicts an example of a stent.

FIG. 1 depicts an example of a stent 100. Stent 100 has a cylindrical shape and includes a pattern with a number of interconnecting structural elements or struts 110. In general, a stent pattern may be designed so that the stent can be radially compressed (crimped) and radially expanded (to allow deployment). The stresses involved during compression and expansion are generally distributed throughout various structural elements of the stent pattern. The present invention is not limited to the stent pattern depicted in FIG. 1.

A stent such as stent 100 may be fabricated from a polymeric tube or a sheet by rolling and bonding the sheet to form a tube. A stent pattern may be formed on a polymeric tube by laser cutting a pattern on the tube. Representative examples of lasers that may be used include, but are not limited to, excimer, carbon dioxide, and YAG. In other embodiments, chemical etching may be used to form a pattern on a tube.

Sterilization is typically performed on implantable medical devices, such as stents and catheters, to reduce the bioburden on the device. Bioburden refers generally to the number of microorganisms that contaminate an object. The degree of sterilization is typically measured by a Sterility Assurance Level ("SAL"), referring to the probability of a viable microorganism being present on a device unit after sterilization. A sterilization dose can be determined by selecting a dose that provides a required "SAL". The required SAL for a device is dependent on the intended use of the device. For example, a device to be used in the body's fluid path is considered a Class III device. SALs for various medical devices can be found in materials from the Association for the Advancement of Medical Instrumentation (AAMI) in Arlington, Va. In one embodiment, the sterility assurance level for biodegradable stents is at a radiation dose from about 20 kGy to about 30 kGy.

Figure 2:
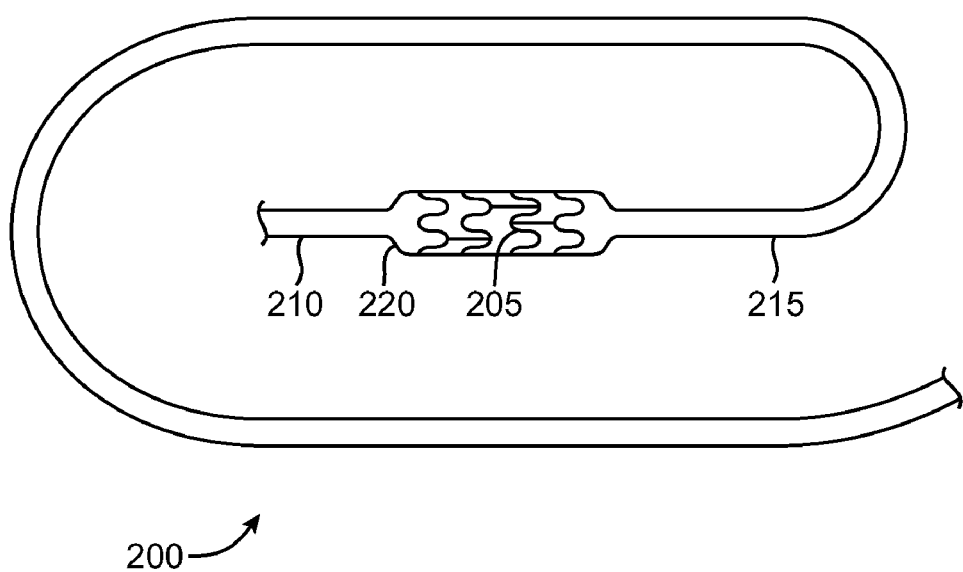
FIG. 2 depicts a stent-catheter assembly.

A stent is typically sterilized after being mounted onto a delivery system or device, such as a catheter. Stents are also typically sterilized, packaged, stored, and transported in a "ready to implant" configuration in which the stent is disposed at the distal end of a catheter. However, the methods described are not limited to sterilizing a mounted stent. FIG. 2 depicts a stent-catheter assembly 200 with a stent 205 disposed on a distal end 210 of a catheter 215. Stent 205 can be crimped over a balloon 220. Stent-catheter assembly 200 may be packaged prior to or after radiation sterilization. Various embodiments herein describe sterilization after stent-catheter assembly 200 is packaged.

The embodiments described herein may be used for sterilizing various kinds of devices, such as an implantable medical device, in particular a stent-catheter assembly. In one embodiment, the device, as described above, can also be enclosed in a container or package. The container or package can include a sealable flexible metallic or plastic pouch that is conventionally used for storage and shipping a stent-catheter assembly. Generally, the pouch protects the assembly from exposure to air, moisture, and light.

In an embodiment, a container or package of a stent-catheter assembly includes a chipboard box and a pouch that is disposed within the box. Typically, stent-catheter assemblies are sterilized after packaging by methods such as E-beam sterilization. A packaged stent-catheter assembly is supported on a fixture during sterilization. The fixture is typically moved on a conveyer arrangement past a radiation beam from a radiation source in a manner that the radiation beam is directed onto the stent-catheter assembly. Alternatively, the radiation source can be moved with respect to the fixture.

In a cold E-beam sterilization process, the stent-catheter assembly can be cooled prior to and/or after sterilization. Additionally or alternatively, the temperature of the stent-catheter assembly can be controlled at a reduced temperature during E-beam sterilization. The stent-catheter assembly can be cooled to a reduced temperature below an ambient temperature which can refer to a temperature between about 15-30° C. In various embodiments, reduced temperature can be less than 10° C., 0° C., −15° C., −25° C., −40° C., −70° C., −100° C., −150° C., −200° C., −240° C., or less than −270° C. The stent-catheter assembly can be cooled by various methods. For example, the cooling prior to sterilization can be performed by disposing the stent-catheter assembly in a freezer for a time sufficient to cool the stent-catheter assembly to a desired temperature.

FIG. 3(a) depicts a schematic illustration of a front view of a fixture 310 supporting two packages 320, each containing a stent-catheter assembly 305 having a stent 330 and catheter 340. Packages 320 can be, for example, a chipboard box containing the stent-catheter assembly disposed within a pouch. FIG. 3(b) depicts an overhead view of fixture 310 of FIG. 3(a) containing packages 320.

In some embodiments, fixture 310 in FIG. 3(b) can be moved as shown by an arrow 325 past a stationary E-beam source that directs an E-beam perpendicular to the face of packages 320, the face being perpendicular to the plane of the page. As shown, a beam 345 is directed perpendicular to the faces of packages 320. The cross-section of the E-beam is circular or generally circular in shape, as depicted by a pulse 342 of an E-beam. In such embodiments, the E-beam is moved up and down as shown by an arrow 343 to irradiate fixture 310 and assemblies 305 along an axis from position X to position Y. Thus, as fixture 310 is conveyed in the direction shown by arrow 325, the entire fixture and assemblies 305 can be irradiated. In some embodiments, the beam pulses up and down 50-70 times, or more narrowly, 64 times a second.

Figure 3C:
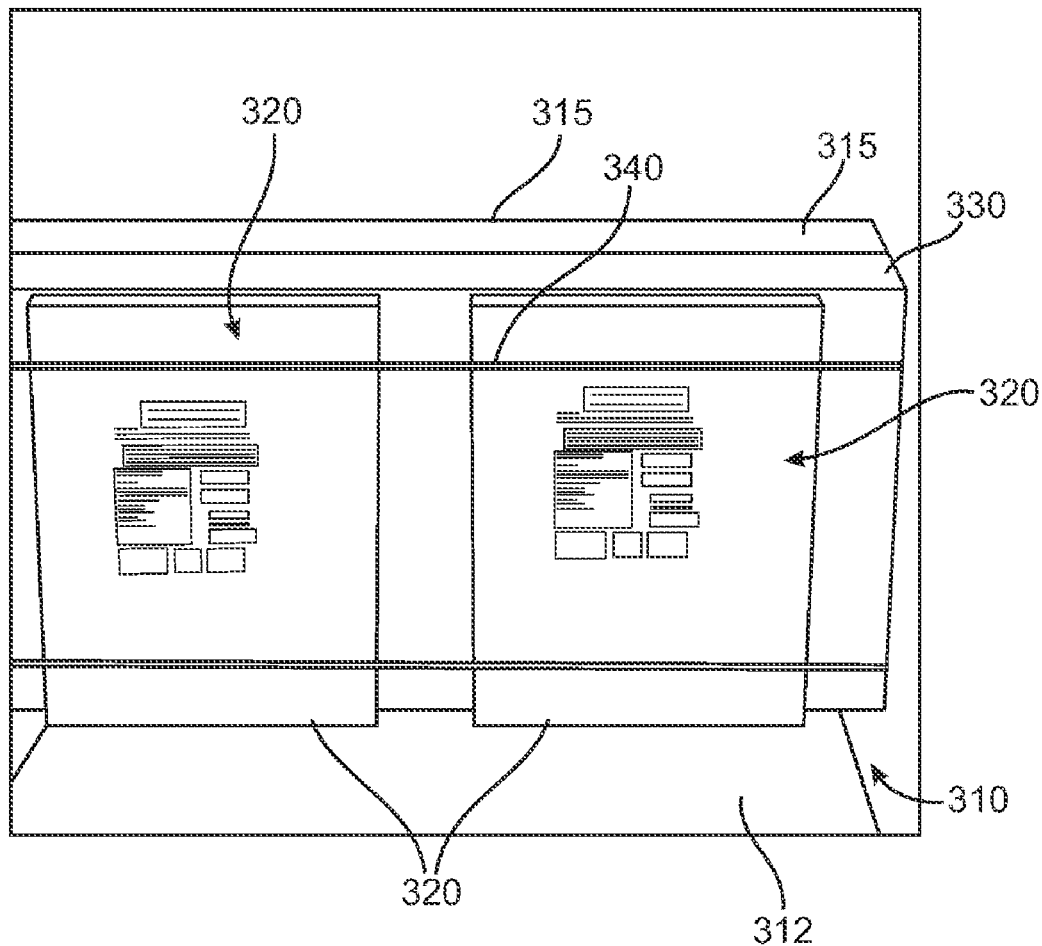
FIG. 3(c) depicts a photograph an overhead view of a fixture supporting two chipboard boxes.

FIG. 3(c) depicts a photograph of front view of fixture 310 supporting two chipboard boxes 320. Fixture 310 includes a metal plate 312 and a support arm 315 that supports boxes 320. Behind chipboard boxes 320 is a foam slab 330. Behind foam slab 330 is support arm 315 of fixture 310 that supports boxes 320. Chipboard boxes 320 are held onto support arm 315 of fixture 310 by fasteners 340. Chipboard boxes can include a stent-catheter assembly that is encased in a pouch (not shown).

In such an arrangement shown in FIGS. 3(a)-3(c), sufficient sterilization of the stent-catheter assembly 305 may require more than one pass past the radiation source. Thus, stent-catheter assemblies 305 can be irradiated with two passes, one pass for exposing one side of the assemblies, and the other pass for irradiating the other side of the assemblies.

With reference to FIG. 2, catheter 215 of stent-catheter assembly 200 may be able to sustain radiation exposure to 50 kGy since the performance of a catheter is less sensitive to radiation exposure. However, the performance of a stent, such as stent 205, is more sensitive to degradation by high radiation doses, in particular a stent having a polymer substrate and/or a polymer coating. High radiation doses can adversely affect the chemical and mechanical properties of a polymer in the stent which can affect its therapeutic functions. For example, if a dose of 25 kGy is desired to be delivered to the stent-catheter assembly 200, two doses of 12.5 kGy are delivered to the device per pass in order to avoid over-exposing the stent to radiation. After irradiating the first side with 12.5 kGy of radiation by focusing the E-beam directly on the package as described, the packages are flipped over to the other side, and irradiated with the remaining 12.5 kGy of radiation.

Sterilization of two devices with two passes of radiation is time consuming, and thus, reduces manufacturing efficiency and throughput. An exemplary fixture may allow only two devices to be sterilized at a time using two passes, one for the front and the other for the back of the devices. The devices can be cooled prior to the second irradiation step to reduce or eliminate chemical and/or mechanical degradation of the polymer of the stent caused by high radiation doses. Thus, sterilization of two devices with two passes of radiation is even more time consuming when the devices must be cooled in between passes of radiation. In some embodiments, the cooling time can be several hours, for example, 12 hours. Thus, cooling before the first pass can be 12 hours, cooling after the first pass can be 12 hours, and cooling after the second pass can be 12 hours.

Additionally, it is desired to deliver a radiation dose to a device in a predictable, narrow range. In this way, reproducibility of the dosage from device to device may be achieved. As described above, one or two devices may be irradiated during one pass of radiation. Such methods of sterilization are limited in their capacity to deliver consistent doses with a narrow range of radiation exposure from device to device.

In the embodiments described herein, multiple devices can be irradiated and sufficiently sterilized with one pass of irradiation. In such embodiments, the orientation of the devices on the fixture in relation to the beam (e.g., the orientation of the face of the package in FIG. 3(a) with respect to the beam) and the position of radiation shields on the devices enable multiple devices (not just two) to be sterilized in one pass of radiation. Since multiple devices are sterilized in one pass, both processing time and throughput are increased compared to the methods illustrated in FIGS. 3(a)-(c). In addition, all of the devices on the fixtures are irradiated substantially uniformly, such that the range of the radiation dose from device to device is very narrow and consistent. Thus, reproducibility of radiation dose from device to device is increased. By increasing reproducibility of radiation dose, fewer devices fall outside a desired SAL range. Also, sterilizing multiple devices in one pass of radiation eliminates the need to cool the devices between passes, further reducing manufacturing time and increasing throughput.

Thus, the embodiments provide a method and apparatus for sterilizing multiple devices at once. Multiple devices are positioned on a fixture during the single pass of radiation so that all of the devices are exposed to a radiation in such a way that the radiation dose from device to device falls within a narrow range. As a result, the methods and apparatus provide good reproducibility from device to device.

Figure 4A:
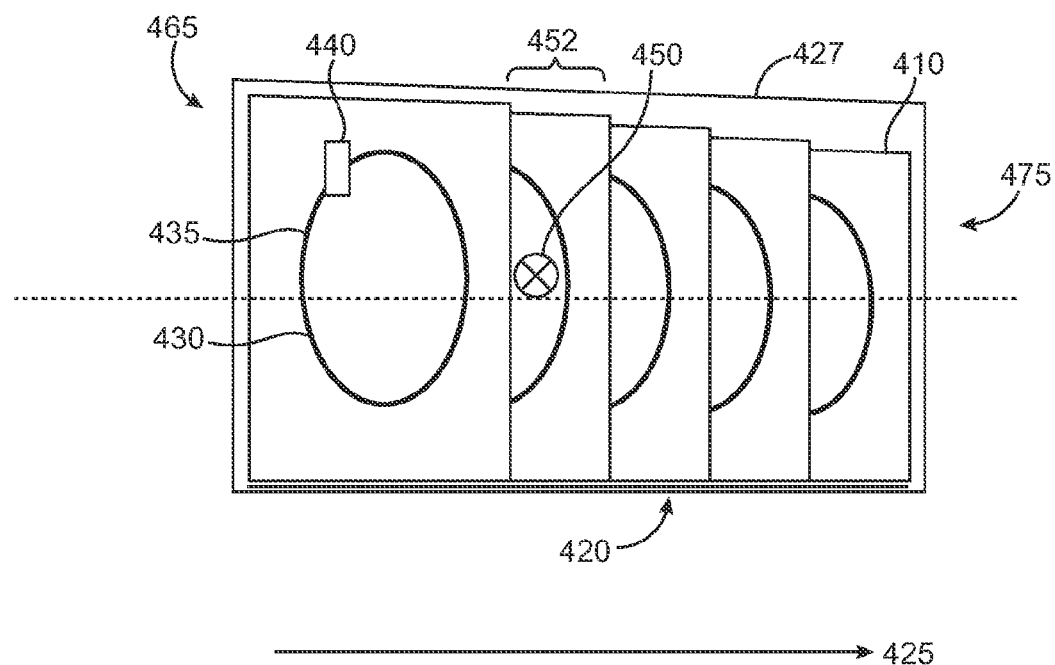
FIG. 4(a) depicts a schematic illustration of a front view of multiple packages supported by a fixture, each package containing a stent-catheter assembly.
Figure 4B:
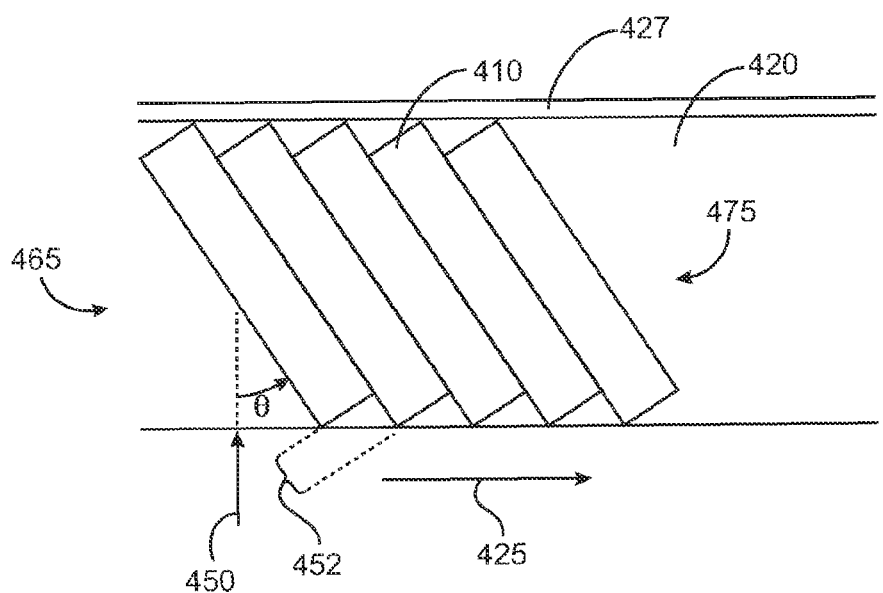
FIG. 4(b) depicts an overhead view of the fixture of FIG. 4(a).

FIGS. 4(a)-(d) illustrate schematic embodiments of the present invention. FIG. 4(a) depicts a schematic illustration of multiple packages 410 supported by a fixture 420, each package containing a stent-catheter assembly 430 that includes a stent 440 mounted on a catheter 430. Packages 410 are stacked horizontally on fixture 420. FIG. 4(b) depicts an overhead view of FIG. 4(b) of multiple packages 410 supported by a fixture 420. Additionally, fixture 420 can include a support element or side arm 427 that supports the stacked packages 410. Support element 427 can be metallic, for example, aluminum.

Packages 410 are staggered so that there is a non-overlapping portion 452 between adjacent packages. As a result, packages 410 are positioned so that the face of the packages is at an acute angle, θ, relative to the direction of the radiation beam 450. In one embodiment, packages 410 are positioned such that θ is between 35-45 degrees, or more narrowly 45 degrees. Fixture 420 in FIGS. 4(a) and 4(b) can be moved as shown by an arrow 425 past the stationary E-beam source that directs an E-beam at an angle θ to the face of packages 410. An arrow 450 shows the E-beam source in FIG. 4(b). The arrangement depicted in FIGS. 4(a) and 4(b) allows sterilization of multiple devices in one pass. Because devices are at an acute angle to beam 450 and staggered on fixture 420, radiation beam 450 penetrates several devices as fixture 420 moves as shown by arrow 425.

As shown in FIGS. 4(a)-(b), devices near a front end 465 of the stack of packages 410 have less shielding from radiation than those further behind. As a result, the radiation exposure to the devices near the front end of the stack can be different that those further behind that have more shielding since radiation exposure varies with depth of penetration and density, as described below. The difference in shielding can result in a variation in radiation exposure due to incoming radiation from device to device.

Additionally, backscattering of radiation from metallic support element or side arm 427 to packages 410 and devices contained within can increase the radiation exposure to the devices. Backscatter of radiation, such as electrons, is caused when the electrons hit a dense material (such as a metallic fixture) and are reflected back. The exposure due to backscatter can be desirable since the portions of the device closer to side arm 427 have reduced radiation exposure since radiation exposure varies with penetration depth, as described below. The backscatter of at least some radiation compensates for the reduced exposure. However, as shown in FIG. 4(a)-4(b), devices at a back end 475 of the stack of packages 410 have more shielding from the backscatter those closer to the front.

The difference in shielding can result in a variation in radiation exposure from device to device due to backscatter.

In general, the thicker and/or denser a material is, the more it will scatter electrons, creating a "shadow" or lower dose area behind the dense material. In one embodiment, the densest part of fixture is placed towards the back to prevent it from shadowing other parts of the device. For example, as pictured in FIG. 5, the densest part of fixture 420 is aluminum side arm 427, which is positioned such that it is behind assemblies 410 relative to beam 450.

Figure 4C:
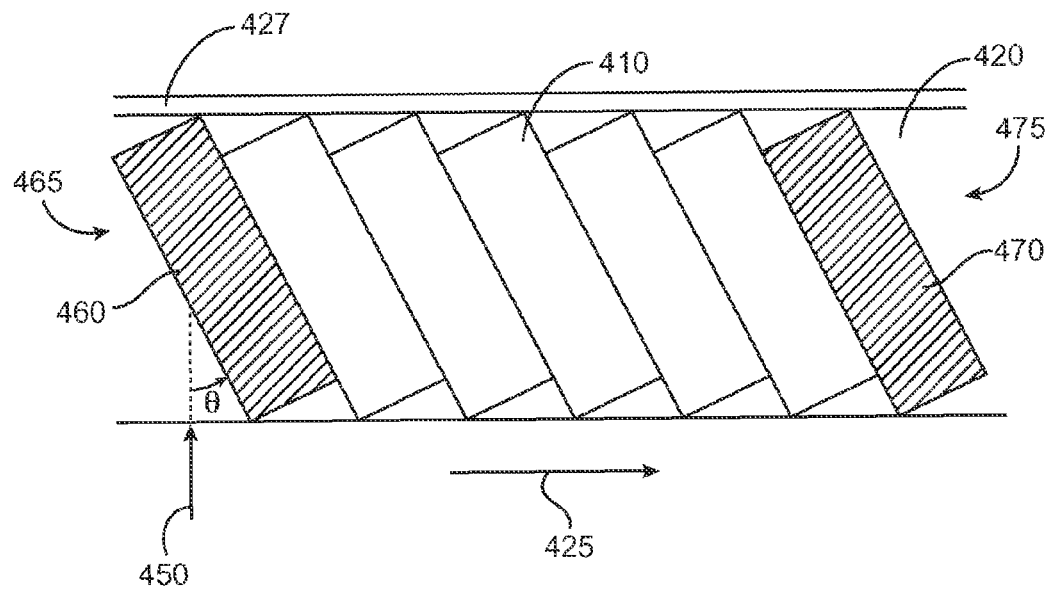
FIG. 4(c) depicts an overhead view of the fixture of FIG. 4(a) additionally including two radiation shields on the front and back of the fixture.
Figure 4D:
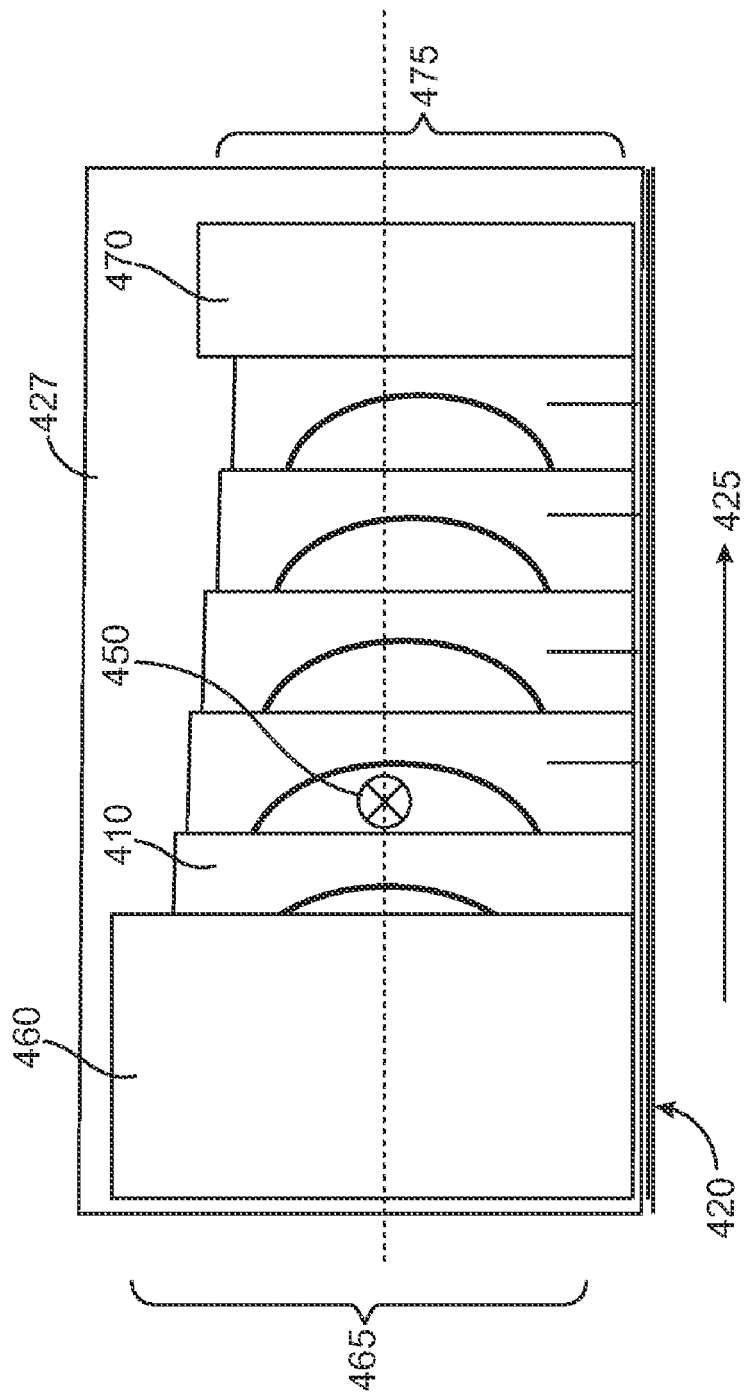
FIG. 4(d) is a schematic illustration of a front view of the fixture of FIG. 4(c).

FIG. 4(c) depicts an overhead view of a system similar to FIG. 4(a) of a multitude of packages supported by a fixture 420, additionally including two radiation shields 460 and 470 on at front end 465 and back end 475 of the stack of packages 410, respectively. FIG. 4(d) is a schematic illustration of a front view of the embodiment depicted in FIG. 4(c). In one embodiment, one or both of radiation shields 460 and 470 are composed of foam.

FIG. 4(d) is a schematic illustration of a front view of the fixture of FIG. 4(c). As depicted in FIGS. 4(c) and 4(d), radiation shields 460 and 470 are strategically positioned on front end 465 and back end 475, respectively, of the stack of devices to reduce the radiation exposure variation from device to device. Radiation shield 460 can reduce or eliminate the difference in radiation exposure between devices near front end 465 and those behind due to incoming radiation. Radiation beam 450 can be modified prior to irradiating the devices located near the front end 465 of the stack of devices on fixture 420, thereby providing greater uniformity in radiation exposure to the devices. Radiation shield 460 can act effectively as a "dummy device." In an embodiment, radiation shield 460 can provide shielding so that the devices near the front end receive the same or similar exposure from incoming radiation as devices behind. Since radiation exposure varies with thickness and density, the thickness and density of the radiation barrier can be selected to obtain a desired exposure to devices.

Radiation shield 470 is positioned on the back end of fixture 420 to shield packages 410 from backscatter of the radiation from side arm 427. Radiation shield 470 can reduce or eliminate the difference in radiation exposure between devices near back end 475 and those behind due to backscattering of radiation. Radiation backscattered from side arm 427 can be modified prior to irradiating the devices located near back end 475 of the stack of devices on fixture 420, thereby providing greater uniformity in radiation exposure to the devices. Radiation shield 475 can also act effectively as a "dummy device." In an embodiment, radiation shield 470 can provide shielding so that the devices near the back end receives the same or similar exposure from backscattered radiation as devices at the front end. The thickness and density of the radiation barrier can be selected to obtain a desired exposure to devices.

Thus, one or more radiation shields can increase the uniformity of the dose received over the multitude of devices positioned on fixture 420. All devices on fixture 420 can be adequately sterilized during one pass of radiation, which can increase throughput. Additionally, in a reduced temperature sterilization process, the cooling step between passes is eliminated in a one pass process, which also reduces process time.

Figure 5:
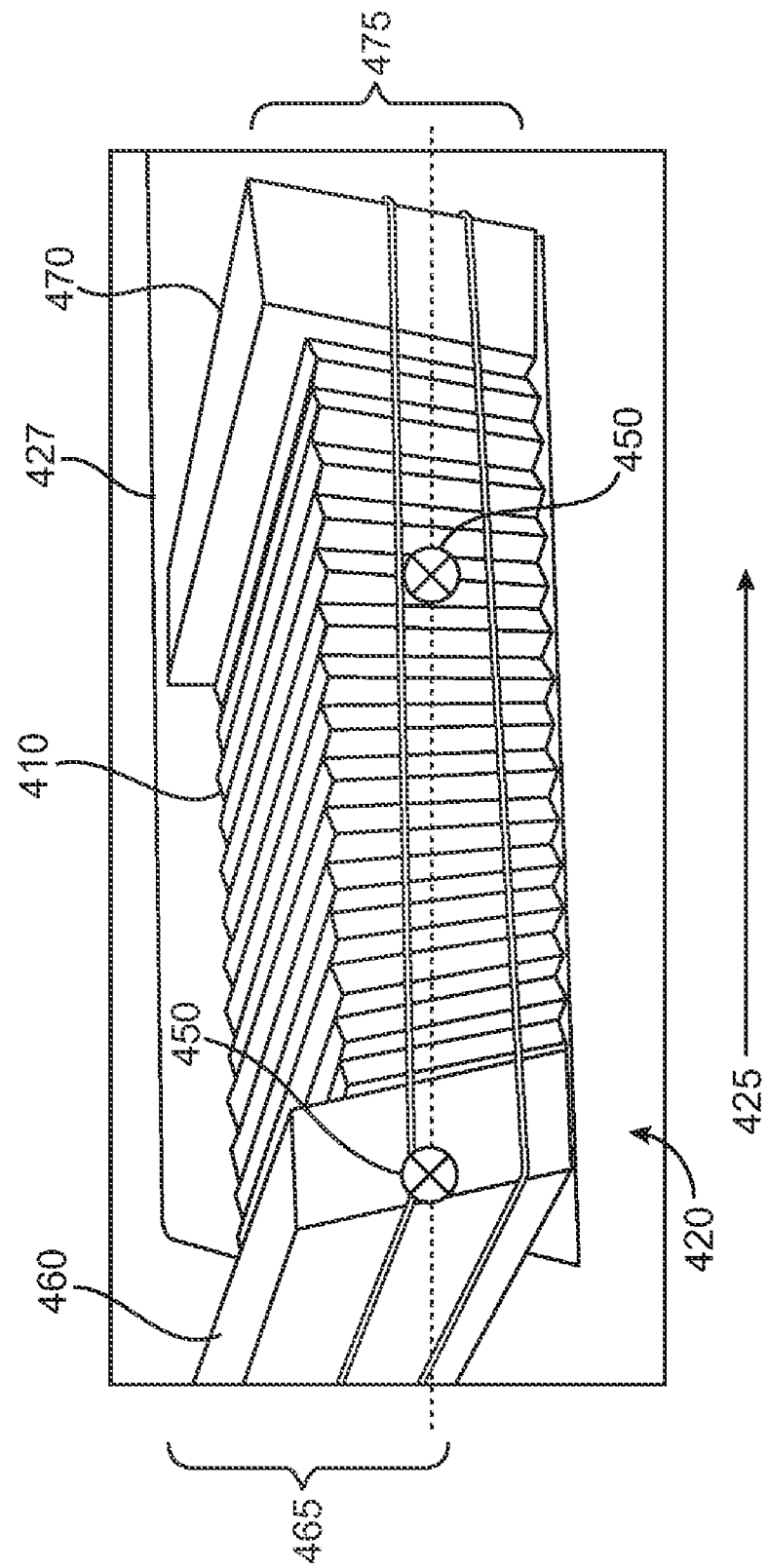
FIG. 5 depicts a photograph of multiple packages supported on a fixture and two radiation shields on the front and the back of the fixture.

FIG. 5 depicts a photograph of a fixture with a multitude of devices with radiation shield 460 and radiation shield 470. An aluminum side arm 427 behind the stacked packages 410 supports the packages. Metal side arm 427 ensures that the packages are positioned on fixture 420 at an angle.

In one embodiment, as depicted in FIG. 5, fixture 420 contains between 12-18 devices. In such embodiments, the radiation beam can penetrate through one to 8 packages, or more narrowly, the radiation beam can penetrate through five packages. It should be understood by those skilled in the art that fixture 420 can contain more or less devices, depending on the size of the device, the fixture, and the angle that the devices are positioned on the fixture.

The dose is selected according to the devices to be sterilized. For example, a desired dose for a stent can be about 25 kGy. In one embodiment a dose of incoming radiation can be set at 35-45 kGy, or more narrowly, 40 kGy. The radiation dose received a stent can be lower than the incoming radiation due to modification of the radiation as it passes through packaging, devices, shielding, etc., as described below. Other radiation doses can be used, depending on the device to be sterilized.

Figure 6:
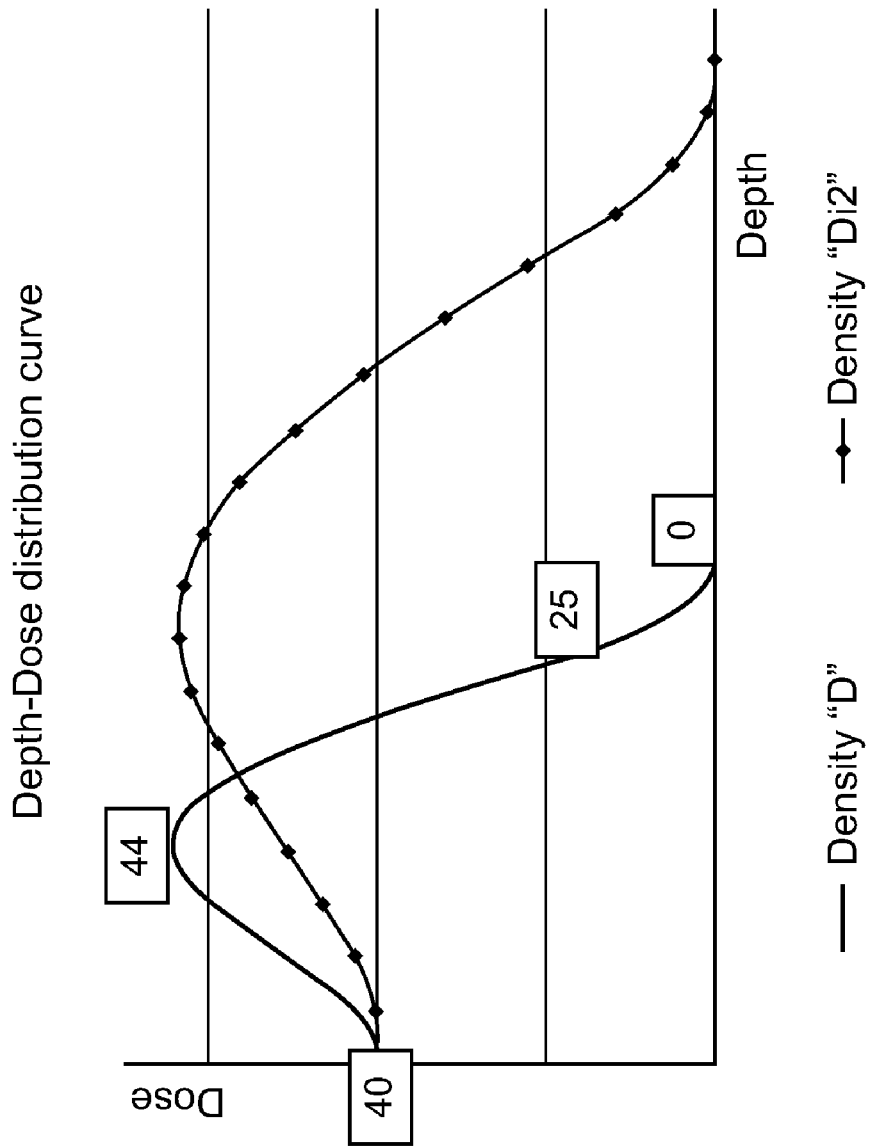
FIG. 6 depicts a depth to dose distribution curve illustrating the relationship between radiation exposure and depth of penetration of a radiation beam.

FIG. 6 depicts a depth dose distribution curve illustrating the relationship between radiation exposure and depth of penetration of the radiation beam for materials with two densities. The curve shows the dose versus the depth of a material that the electrons travel through for two densities. As depicted, the dose initially rises and then drops off. For example, if a device is irradiated with 40 kGy, the peak dose is at 44 kGy, and it eventually drops down to, for example, 25 kGy and finally to 0 kGy upon further permeation through a material. As shown in FIG. 6, the curve is shifted to larger penetration as density is decreased.

The general relationship in FIG. 6 can be used to design a fixture, arrangement of devices, and shields in a manner that devices received a desired radiation dose. The total exposure to a device can be from incoming radiation and backscattered radiation. Thus, packages can be arranged, as described above, and the thickness and density of the shields can be selected to obtain a desired radiation exposure. As discussed above, the shields can be selected to increase the uniformity of exposure from device to device. In alternate embodiments, the total exposure can be due to incoming radiation, with no exposure due to backscattering.

The curve in FIG. 6 can be manipulated by the radiation shields to obtain a desired dose level. The radiation shields having a certain density, like foam, are used to change the radiation dose to a desired level in a specific depth of irradiated packages. Increasing the density shifts the peak to a smaller depth, thus, larger depths have a smaller dose. By adding radiation shields at both ends of a fixture, as pictured in FIG. 5, the density dose curve advances to the descending portion of the curve prior to irradiating the fixtures, thereby reducing radiation absorption of the device. In this way, devices on the ends of the stack are substantially consistent with the radiation absorption of the other devices that are shielded by other devices.

Thus, radiation shields can reduce the dose of radiation that the devices are irradiated with by shifting the dose to depth curve. Since the packages are at an angle with respect to the beam, the radiation exposure varies at least as a function of "x" (FIG. 7) across the face of the device, and more generally as a function of the "x" and "y" position on the face of the device. Thus, to have the same exposure for each stent, the stents may be positioned to the same x position, or more generally at the same position on the face of the device. The position can be selected so that the stents receive a desired radiation exposure.

Figure 7:
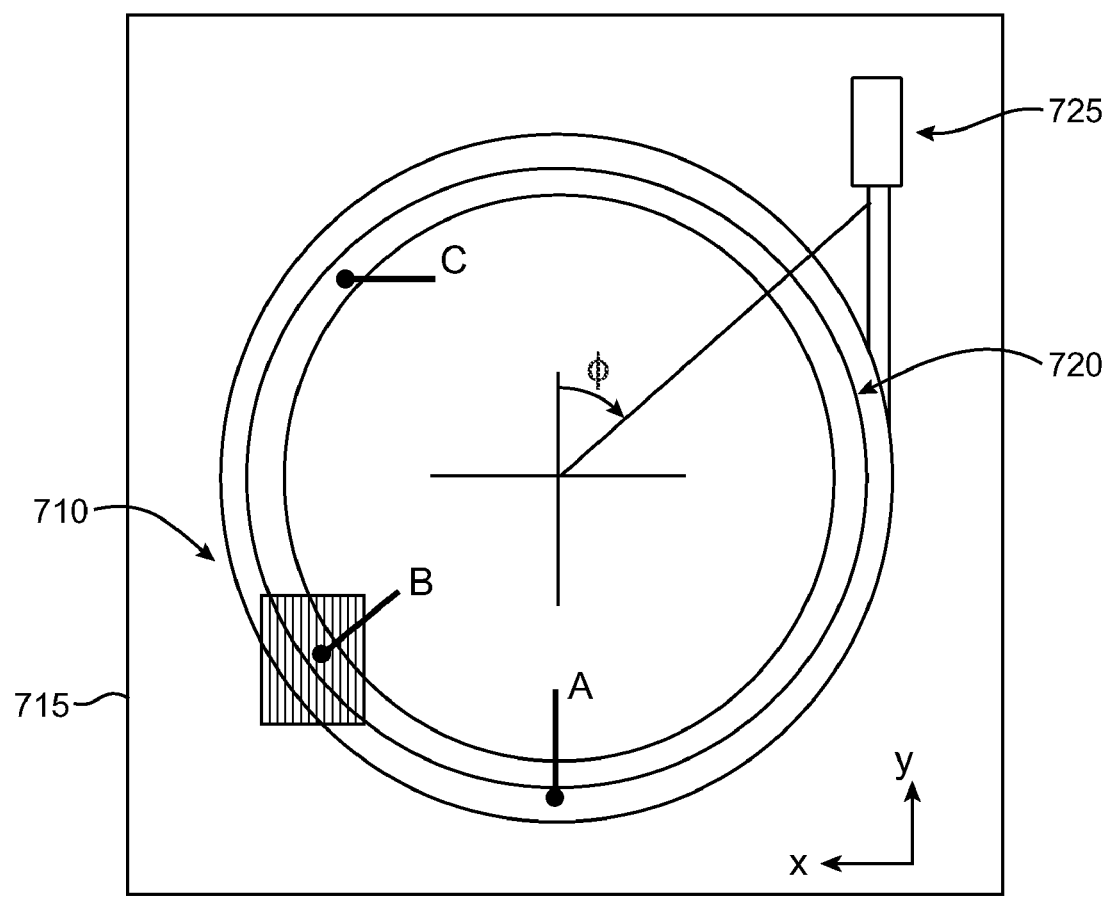
FIG. 7 depicts a package for a stent-catheter assembly, indicating three areas of the package that are measured for radiation dose mapping of a device.

As depicted in FIG. 7, a stent-catheter assembly 710 with a stent 725 disposed on a catheter 720 can be inside a storage package 715. Devices are positioned on fixture such that stents are at an angle $\phi$. In one embodiment, devices are positioned such that each stent is positioned at the same angle $\phi$ in each package to increase the uniformity of exposure to the stent from device to device. In one embodiment, stent 725 may be positioned in a package 715 on a fixture such that stent 725 is at a 7 o'clock ($\phi=216°$) position when viewing stent 710 from the front of the fixture. Stents may be positioned within package 715 on the fixture in other angles, such that it is between 1 and 3 ($\phi=36-108°$), or more narrowly, at a 2 o'clock ($\phi=72°$) position when viewing stent 725 from the front of fixture.

At various parts of the stent, radiation dose requirements may differ. However, when sterilizing multiple stent-catheter assemblies, it is preferable that the radiation dose at the stent not vary substantially from stent to stent since E-beam exposure affects properties of a material. The radiation dose received by a stent should be within a narrow range from stent to stent. At the catheter 720, a tolerance for a variation in radiation exposure is higher. The radiation exposure, for example, can be between at 20-50 kGy because the catheter is more robust than the stent for example. In contrast, the performance of a balloon, over which a stent is disposed, is much more vulnerable to degradation, thus it is desirable for its exposure to be at less than 40 kGy. Performance of stent 710 and balloon 725 are more sensitive to changes in properties, and thus, radiation exposure. Performance of catheter 720 is less sensitive to various properties, so a greater variation of radiation exposure for the catheter is more tolerable.

Dose mapping may be used to monitor the range of radiation dose received by selected portions of irradiated devices. Dose mapping refers to measuring radiation exposure at specific areas of an irradiated package and device within the package. FIG. 7 depicts three areas A, B, and C where the radiation may be measured.

Figure 8:
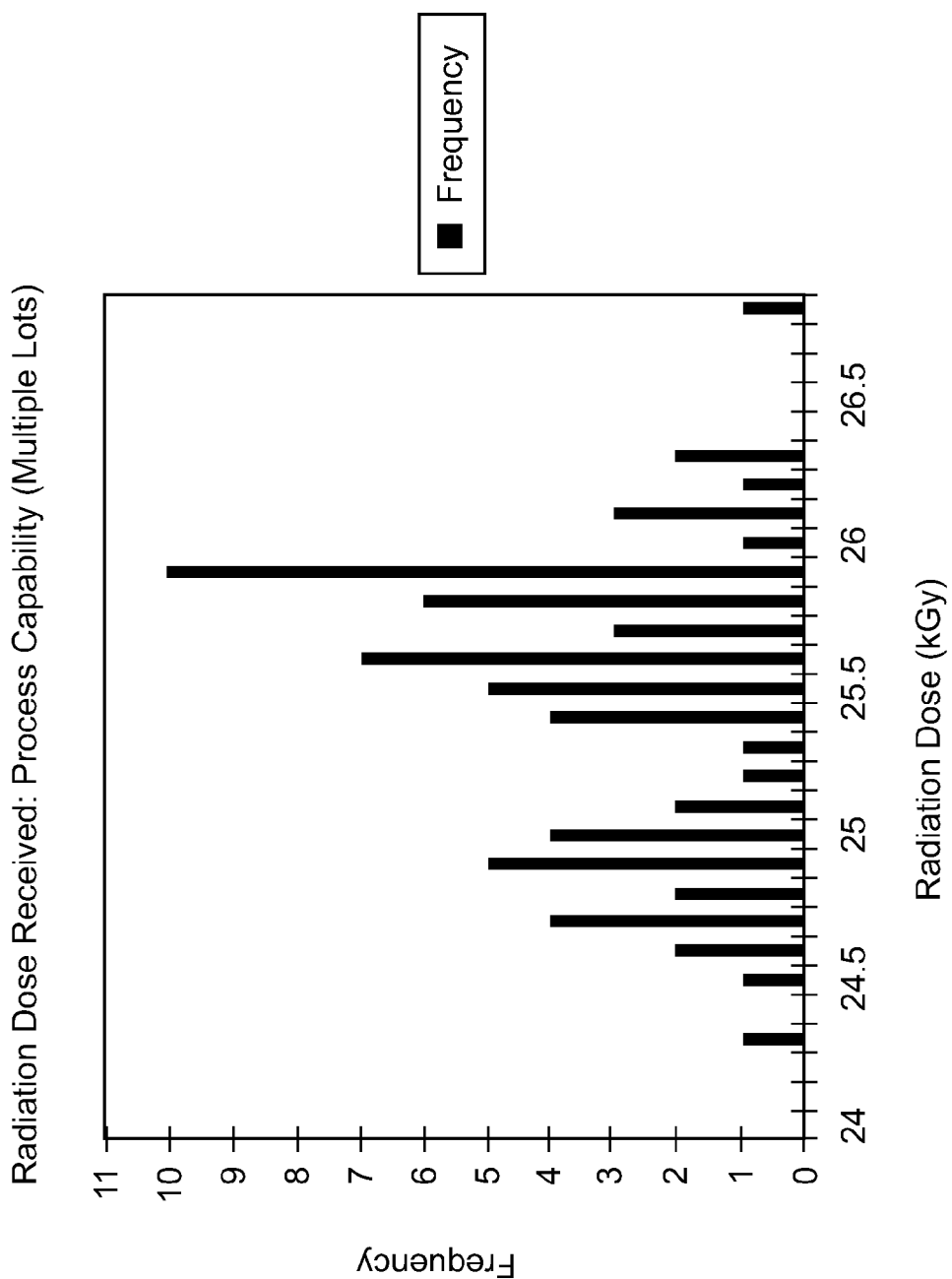
FIG. 8 depicts a chart illustrating the radiation dose received by multiple lots of chipboard boxes, each containing a stent-catheter assembly.

FIG. 8 depicts a chart illustrating the radiation dose received by multiple lots of chipboard boxes, each containing a stent-catheter assembly. The system for sterilization is as depicted in FIG. 5. Each lot corresponds to 15 chipboard boxes that are exposed to one pass of radiation. The radiation dose corresponds to the radiation exposure at a particular region of each stent in each lot. The radiation dose received by a particular area of the stents that are packaged and irradiated are compared to multiple lots as illustrated by the graph. As indicated, the spread of radiation ranges from 24.3 to 26.8, with the frequency of doses being much higher in the 24.7 to 26.2 range. Thus, most devices are of a very narrow range of about 24 to 26 KGy. Providing a narrow dose range prevents irradiating devices outside their required SAL, outside of a defined tolerance, or both. The likelihood of exposing a par of a device to radiation outside a desired SAL is reduced.

In one embodiment, devices are irradiated at a reduced temperature and "Targeted Dose" process. The device may be cooled prior to, during, or after sterilization. The stent can be cooled in a variety of ways, including, but not limited to, cooling the stent in a freezer, blowing a cold gas on the stent, placing the stent in proximity to a cold medium such as ice, dry ice, freezable gel, liquid nitrogen, etc.

The storage package for the implantable medical device, such as a stent, can be designed in any convenient form, shape and size that permits the effective enclosure of a stent contained therein. For example, a flexible pouch made from a polymer, glass, ceramic, metallic substance, or a combination thereof. Package can be made from metal, foam, plastic etc. For example, a material with micro-voids, such as foam, or particles, can scatter E-beam radiation which results in the more even distribution. "Foam" can refer to a polymer foam, for example, polystyrene foam such as Styrofoam from Dow Chemical Company, Midland, Mich. Thus, the package material can also be made of a material that distributes radiation more uniformly such as foam.

The package may be compact and shaped so as to minimize storage space occupied by the package. For example, without limitation, the package can be in the shape of a tube, box or a pouch. In one embodiment, the package can have a rectangular cross-section with a width between 8 in and 12 in and a length between 10 in and 13 in. Also, depending on the types of substance(s) used to construct the package, the package can be of various degrees of rigidity or flexibility.

Such packages can be stored individually or stored together with other packaged stents. For example, a pouch can be disposed in a box, such as chipboard box. The chipboard box can then be stored individually or along with a number of similar or identical packages including stents.

The package may be made of a metallic substance, the package for example can be formed of a metallic film. Suitable examples of films include, but are not limited to, gold, platinum, platinum/iridium alloy, tantalum, palladium, chromium, and aluminum. Suitable materials for the package may also include oxides of the above-mentioned metals, for example, aluminum oxide. Medical storage packages may be obtained from, for example, Oliver Devices Company of Grand Rapids, Mich.

A polymer for use in fabricating an implantable medical device, such as a stent, can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed and/or eliminated by the body. The processes of breaking down and absorption of the polymer can be caused by, for example, hydrolysis and metabolic processes. For stents made from a biodegradable polymer, the stent is intended to remain in the body for a duration of time until its intended function of, for example, maintaining vascular patency and/or drug delivery is accomplished.

The device may also be made of a metallic material or an alloy such as, but not limited to, a biodegradable metal.

The device may also include a drug or active agent that can include, but is not limited to, any substance capable of exerting a therapeutic, prophylactic, or diagnostic effect. The drugs for use in the implantable medical device, such as a stent or non-load bearing scaffolding structure may be of any or a combination of a therapeutic, prophylactic, or diagnostic agents. The drug can be incorporated in a polymer substrate or in a coating on the substrate that includes the drug within a polymer carrier.

While particular embodiments of the present invention have been shown and described, it will be obvious to those skilled in the art that changes and modifications can be made without departing from this invention in its broader aspects.

EXAMPLES

Three experiments were performed to map the dose distribution on a biodegradable stent and delivery system using a fixture as depicted in FIG. 4(*b*). For each of the experiments, 15 packages containing stents were stacked onto the aluminum fixture such that the packages were angled 45° to the trajectory of the radiation beam. The delivered dose at a particular region of the stent in each package was measured.

In the first experiment, no radiation shield of foam was positioned at the front end or back end of the fixture. The delivered dose range absorbed by the stents ranged from 15.88 to 20.96 kGy, or a ratio of 1:32.

In the second experiment, a radiation shield of foam was positioned at the front end of the fixture. The results indicated a reduction in the dose spread absorbed by the stents ranged from 22.49 to 25.48 kGy, or a ratio of 1:14. It is believed that the backscatter from the aluminum fixture at the back end was contributing to scatter, and thus, the spread.

In the third experiment, a radiation shield of foam was added to both the front end and the back end of the fixture. In other words, a radiation shield was positioned on both ends of the stack of devices. On the back end of the fixture, the spread of radiation absorbed by the stents ranged from 23.89 to 26.6 kGy, or a ratio of 1:11. This experiment was repeated to confirm the results, having a ratio of 1:05. Thus, a radiation shield positioned at both ends of the stack of devices on the fixture provided the narrowest spread of radiation dose among the devices positioned on the fixture.

The invention claimed is:

1. A method of radiation sterilizing a plurality of stent-catheter assemblies, the method comprising:
    positioning a plurality of stent-catheter assemblies on a fixture, each stent-catheter assembly being in a planar configuration within corresponding packages supported on the fixture, each package including a planar front surface and a planar back surface, wherein the packages form a stack in which the planar front surface of each package is disposed against the planar back surface of another of the packages, and wherein the stents of the assemblies are positioned at a position in each package such that the stents are exposed to the same or substantially the same radiation; and
    exposing the packages, while on the fixture, to an incoming radiation beam, the radiation beam traveling in a direction at an acute angle to the planar front surfaces, wherein the radiation beam travels toward the planar front surfaces and travels away from the planar back surfaces,
    wherein during the exposing step, the radiation beam defines a radiation exposure area limited to a portion of the stack of the packages.

2. The method according to claim 1, wherein the radiation beam comprises an e-beam radiation beam.

3. The method according to claim 1, wherein the packages in the stack are staggered so that the planar back surfaces partially cover the planar front surfaces.

4. The method according to claim 1, wherein each of the stent catheter assemblies are arranged in a coiled configuration.

5. The method according to claim 1, wherein the incoming radiation is 35-45 KGy and the stent in each of the assemblies is positioned at 36°-108° in the coiled configuration.

6. The method according to claim 1, wherein the acute angle is 35°-45°.

7. The method according to claim 1, wherein the exposing of the packages to the radiation beam comprises movement of the fixture with respect to the incoming radiation beam.

8. The method according to claim 1, wherein the assemblies are cooled prior to, during or after positioning the assemblies on the fixture.

9. A method of sterilizing a stack of packages of medical devices, the method comprising:
    placing a stack of packages of medical devices horizontally on a fixture having a support element, the step of placing the stack including:
        placing the stack between a radiation source and the support element of the fixture,
        staggering the stack of packages so that a back surface of each package is disposed on and partially covers a front surface of another of the packages, and
        positioning the stack of packages so that the front surfaces of the packages face toward and are at an acute angle relative to a radiation beam from the radiation source; and
    exposing the packages, while on the fixture, to an incoming radiation beam, wherein during the exposing step, the radiation beam defines a radiation exposure area limited to a portion of the stack of the packages.

10. The method of claim 9, wherein as a result of the staggering and the positioning, the stack of packages are oriented such that the medical device in each one of the packages is partially covered by an adjacent one of the packages with respect to the incoming radiation beam.

11. The method of claim 10, wherein the medical device in each package comprises a stent.

12. A method of arranging a plurality of stent-catheter assemblies for radiation sterilization, the method comprising:
    arranging each of a plurality of stent-catheter assemblies in a planar configuration within a package;
    stacking the packages horizontally so that a planar back surface of each package is disposed on a planar front surface of another of the packages, wherein the stent of each stent-catheter assembly is positioned at a position in the corresponding package such that the stents are exposed to the same or substantially the same radiation when the packages are radiation sterilized; and
    exposing the packages to an incoming radiation beam, the radiation beam being at an acute angle to the planar front surfaces, wherein the planar front surfaces face the radiation beam and the planar back surfaces face away from the radiation beam,
    wherein during the exposing step, the radiation beam defines a radiation exposure area limited to a portion of the stack of the packages.

13. The method according to claim 12, wherein the packages in the stack are staggered so that the planar back surfaces partially cover the planar front surfaces.

14. The method according to claim 12, wherein each of the stent-catheter assemblies is arranged in a coiled configuration.

15. The method according to claim 12, wherein the incoming radiation is 35-45 KGy and the stent in each of the assemblies is positioned at 36°-108° in the coiled configuration.

16. The method according to claim 12, wherein the acute angle is 35°-45°.

17. The method according to claim 12, wherein the exposing of the packages to the radiation beam comprises movement of the packages with respect to the incoming radiation beam.

18. The method according to claim 12, wherein the assemblies are cooled prior to, during or after the packages are stacked horizontally.

19. A method of arranging a stack of medical device packages for radiation sterilization, the method comprising:
    staggering a stack of packages horizontally so that that a back surface of each package partially overlaps a front surface of another of the packages;
    positioning the stack of packages so that front surfaces of the packages face toward and are at an acute angle relative to a radiation beam, wherein each medical device is in the same horizontal and vertical positions within the package; and followed by
    exposing the packages to an incoming radiation beam, wherein during the exposing step, the radiation beam defines a radiation exposure area limited to a portion of the stack of the packages.

20. The method of claim 19, wherein as a result of the staggering and the positioning, the stack of packages are oriented such that the medical device in each one of the packages is partially covered by an adjacent one of the packages with respect to the incoming radiation beam.

21. The method of claim 20, wherein the medical device in each package comprises a stent.

* * * * *